United States Patent
Nogarin et al.

(10) Patent No.: US 8,343,226 B2
(45) Date of Patent: Jan. 1, 2013

(54) HUMERAL PROSTHESIS

(75) Inventors: Livio Nogarin, Verona (IT); Roberto Rotini, Bologna (IT); Paolo Dalla Pria, Udine (IT)

(73) Assignee: LIMA-LTO SpA, San Daniele del Friuli (IT)

( * ) Notice: Subject to any disclaimer, the term of this patent is extended or adjusted under 35 U.S.C. 154(b) by 222 days.

(21) Appl. No.: 12/666,567

(22) PCT Filed: Jul. 2, 2008

(86) PCT No.: PCT/IB2008/001744
§ 371 (c)(1),
(2), (4) Date: Apr. 9, 2010

(87) PCT Pub. No.: WO2009/004469
PCT Pub. Date: Jan. 8, 2009

(65) Prior Publication Data
US 2010/0211178 A1    Aug. 19, 2010

(30) Foreign Application Priority Data
Jul. 3, 2007  (IT) .............................. UD2007A0122

(51) Int. Cl.
*A61F 2/40* (2006.01)
(52) U.S. Cl. .................................. 623/19.13; 623/19.12
(58) Field of Classification Search ..... 623/19.11–19.14
See application file for complete search history.

(56) References Cited

U.S. PATENT DOCUMENTS

| 7,011,686 B2 * | 3/2006 | Ball et al. ................... 623/19.14 |
| 7,033,396 B2 | 4/2006 | Tornier |
| 7,470,287 B2 | 12/2008 | Tornier et al. |
| 2004/0039449 A1 | 2/2004 | Tornier |
| 2005/0165490 A1 | 7/2005 | Tornier |
| 2005/0288791 A1 | 12/2005 | Tornier et al. |
| 2009/0112328 A1 | 4/2009 | Tornier et al. |

FOREIGN PATENT DOCUMENTS

| EP | 1 380 274 A1 | 1/2004 |
| EP | 1 611 872 A1 | 1/2006 |
| FR | 2 652 498 | 4/1991 |
| GB | 2 405 346 A1 | 3/2005 |
| IT | UD2004A000194 | 4/2006 |
| WO | 2007/122327 A2 | 11/2007 |

* cited by examiner

*Primary Examiner* — Christopher D Koharski
*Assistant Examiner* — Megan Wolf
(74) *Attorney, Agent, or Firm* — Novak Druce + Quigg, LLP

(57) ABSTRACT

A humeral prosthesis, for the articulation of a humerus in a scapula of a shoulder having a glenoid cavity, includes an articulation device able to be associated both with an articulation element mounted on the glenoid cavity, and also at the top of said humerus by an attachment element. The articulation device comprises a first element able to articulate with the articulation element and a second element associated with the attachment element, the first element and the second element being pivoted to each other around a pivoting axis to allow a free relative rotation thereof around the pivoting axis.

20 Claims, 5 Drawing Sheets

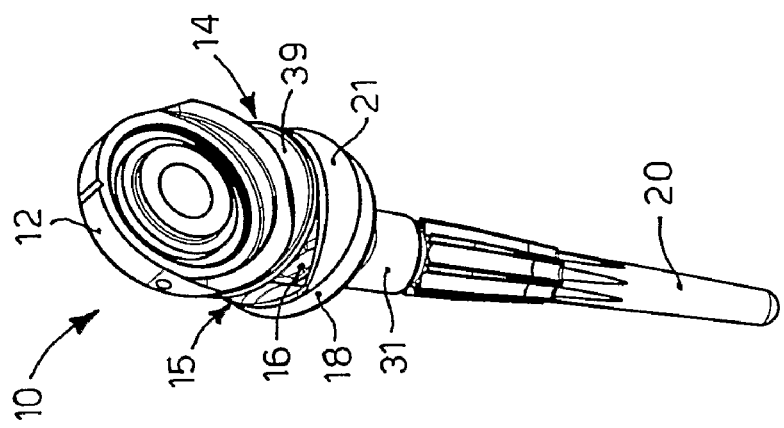
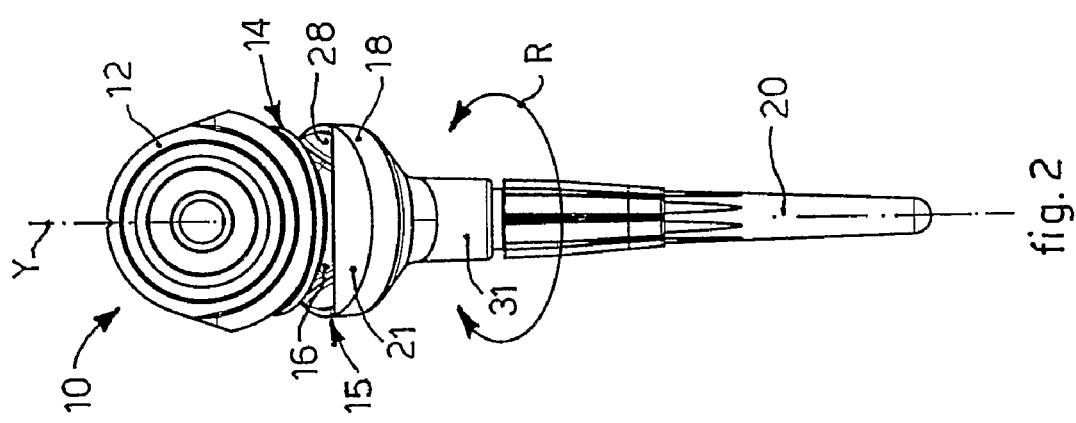
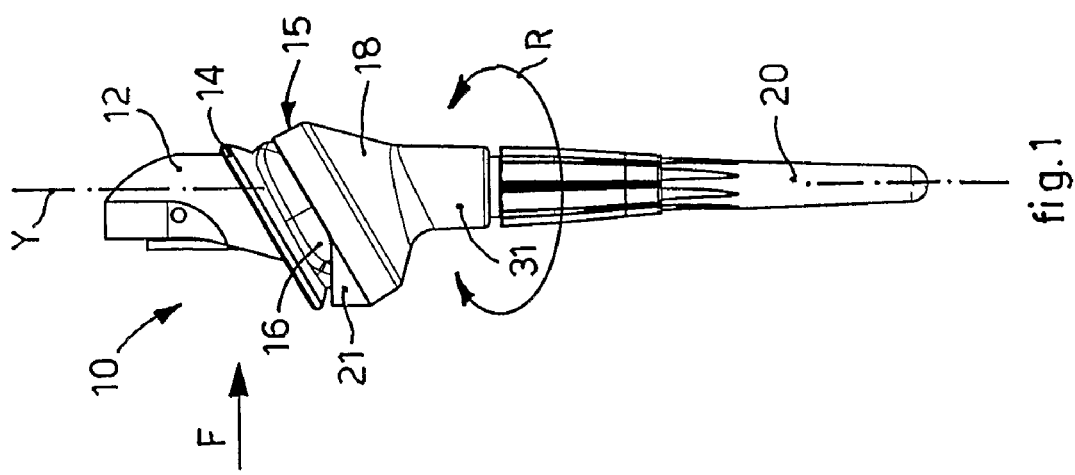

HUMERAL PROSTHESIS

This application is a §371 National Stage Application of International Application No. PCT/IB2008/001744, filed on 2 Jul. 2008, claiming the priority of Italian Patent Application No. UD2007A000122 filed on 3 Jul. 2007.

FIELD OF THE INVENTION

The present invention concerns a humeral prosthesis for the articulation of a shoulder.

The present invention is advantageously applied to a so-called inverse prosthesis, in which a convex-shaped head, or glenosphere, is associated with the glenoid seating of the shoulder and articulates in a concave artificial seating associated with the top of the humerus.

The present invention is also applied to a normal or anatomical prosthesis, in which a substantially semi-spherical head is associated with the humerus and articulates in a mating concave seating, natural or artificial, associated with the glenoid seating.

BACKGROUND OF THE INVENTION

Prostheses of the shoulder are known, which have a first articulation element associated with the meta-epiphysary part of the humerus, and a second articulation element associated with the shoulder.

In particular, in the case of anatomical or normal prostheses, there is a substantially semi-spherical head, mounted on the humerus, which articulates in a mating concave seating, natural or artificial, associated with the glenoid seating of the scapula.

It is also known to use inverse prostheses, which reproduce the gleno-humeral anatomy in an inverse manner, in which there is a humeral cup or insert of the concave type, inserted into the meta-epiphysary part of the humerus, which is able to articulate with a convex element, or glenosphere, fixed to the scapula.

Normally, inverse prostheses are used in cases of serious muscular degeneration of the shoulder, particularly of the rotator cuff muscles.

A fundamental requisite for a prosthesis, whether anatomical or inverse, is that it allows a good articular stability.

Obtaining a good articular stability, apart from the correct positioning of the elements of the prosthesis, which must be identified by the surgeon in an area of very limited size, also depends on the residual rotator cuff muscles and on the articular capsule. In fact, it is necessary to establish, artificially, a dynamic balance with the components of the prosthesis which allows, as much as possible, to recover the normal physiological functions of the shoulder-humerus articulation and which, however, it is difficult to provide.

In both anatomical prostheses and in inverse prostheses, an incorrect positioning of the components of the prosthesis can cause articular instability and contact between the humeral prosthesis and the scapula, with consequent wear of the bone, in the movement of rotation or adduction.

In particular, in anatomical prostheses there may be a risk of wear of the bone tissue due to the rubbing of a part of the prosthesis with the shoulder during the movements of rotation, particularly intra-rotation and extra-rotation.

In inverse prostheses, on the contrary, the typical medialization of the humerus can cause articular instability, which affects 10% of operations, due to the non-appropriate anatomical coupling typical of such prostheses.

In inverse prostheses, we also have the problem of the "scapular notch", due to the wear of the material which constitutes the humeral cup which rubs against the scapula, mainly at the bottom but also at the rear, and the consequent osteolysis of the glenoid.

Normally, to limit some of these problems, inverse prostheses for the shoulder are positioned with zero retroversion, or a low level of retroversion, of the humerus; the first solution increases the risk of rear scapular notch, the second in any case introduces problems of articular instability and impingement with the shoulder.

All in all, therefore, the positioning of the prostheses, both anatomical and inverse, has the problem that the optimum orientation between the humeral component and the glenoid component is always given, or that this orientation is not known in advance.

This entails a compromise choice between articular stability, to be provided as far as possible according to the dynamic balance described above, and the risk of knocking and rubbing against the shoulder.

This often prevents the prosthesis from being positioned in an optimum manner, and consequently introduces risk factors of articular instability, impediment to certain movements, knocking and rubbing.

Purpose of the present invention is to achieve a humeral prosthesis which, once implanted, has the capacity to center itself according to the dynamic conditions of the shoulder-humerus combination, so as to guarantee articular stability, make movements more simple and physiological, and to improve the overall efficiency and the duration over time of the prosthesis.

The Applicant has devised, tested and embodied the present invention to overcome the shortcomings of the state of the art and to obtain these and other purposes and advantages.

SUMMARY OF THE INVENTION

The present invention is set forth and characterized in the independent claim, while the dependent claims describe other characteristics of the invention or variants to the main inventive idea.

The present invention is applied both to an inverse prosthesis and also to a normal or anatomical prosthesis, for the articulation of a humerus in a scapula of a shoulder having a glenoid cavity.

In accordance with the above purpose, a humeral prosthesis according to the present invention comprises an articulation device able to be associated both with an articulation element, mounted on the glenoid cavity, and also with the top of the humerus by means of suitable attachment means.

According to a characteristic feature of the present invention, the articulation device comprises a first element able to articulate with the articulation element and a second element able to be associated with said attachment means.

The first element and the second element are pivoted to each other around a pivoting axis in order to allow a free relative rotation between them around the pivoting axis.

In a variant of the invention, the pivoting axis advantageously coincides with the so-called diaphysis axis defined by the humerus and therefore said pivoting allows the free rotation of the first and second element of the articulation device particularly in the movements of intra-rotation and extra-rotation.

According to possible operative, physiological or anatomical requirements, the pivoting axis can be parallel but not coincident with the diaphysis axis.

Another variant provides that the pivoting axis is inclined by a pre-determined angle with respect to said diaphysis axis, again in order to meet particular needs.

In the case of inverse prostheses, the articulation element is of the convex type, the so-called glenosphere, and the first element is consequently of the concave type, the so-called humeral cup.

In the case of anatomical prostheses, the articulation element is of the concave type, the so-called glenoid cavity, artificial or natural, and the first element is consequently of the convex type, the so-called humeral head.

With the present invention the humeral prosthesis, once implanted, has the capacity to center itself according to the dynamic conditions of the shoulder-humerus combination, dynamically moving to the optimum orientation between the humeral component and the glenoid component, guaranteeing articular stability and making movements more simple and physiological, advantageously the movements of intra-rotation and extra-rotation.

Furthermore, the present invention reduces or eliminates the risks of wear on the bone due to rubbing between the shoulder and components of the prosthesis, thus improving the overall efficiency and the duration in time of the prosthesis.

In fact, the present invention provides that the movements of intra-rotation and extra-rotation of the humerus are entrusted to the pivoting of the first and the second element of the articulation device, thus freeing the articular coupling of the shoulder and the articulation device from this task.

This allows the surgeon more degrees of freedom in choosing the reciprocal position of the articulation element fixed to the shoulder and the humeral component of the prosthesis.

A variant of the present invention provides that the relative rotation allowed by the pivoting of the first element and the second element is limited to a pre-determined angle of rotation.

This can be achieved, according to a variant, by providing limiting elements to limit the rotation, associated with the first and second element of the articulation device.

According to a variant, the first element and the second element have respectively a convex portion and a concave portion, able to couple with each other.

Advantageously, the surfaces of the convex and concave portions are shaped so as to be at least partly complementary with each other, in order to define substantially congruent abutment walls which cooperate in a determinate angular interval and to function, they too, as elements to limit the rotation.

It is clear that, according to another variant, there may be a geometric inversion of the coupling between the first element and the second element of the articulation device, with the convexity on the second element and the concavity on the first element.

In these variants, the humerus is free to rotate around the pivoting axis, centering itself and adapting on each occasion to the dynamic balance that is established, in the determinate angular range, around the pivoting between the first element and the second element of the articulation device.

Once the pre-established angular limit is reached, with abutment between the first and the second element, any further intra-rotation or extra-rotation determines the start of the normal articulation between the humeral component and the glenoid component of the prosthesis.

In fact, there is a solid rotation of the whole articulation device, like a single body, which thus articulates, in a traditional manner, with respect to the glenoid component.

These variants maintain the advantages of a good freedom of reciprocal positioning of the humeral and glenoid components of the prosthesis, typical of the main inventive idea, also in cases of serious physiological muscular deficit, guaranteeing, especially in such cases, articular stability of the components of the prosthesis, particularly the coupling and pivoting of the first and second element of the articulation device.

Moreover, in the case of inverse prostheses, the present invention allows to position the humeral component with a low degree of retroversion, in order to increase the degree of intra-rotation, also eliminating the known problems in said solution of articular instability and impingement with the shoulder.

The present invention, applied to a normal or anatomical prosthesis, allows to reduce the risk of wear on the bone tissue due to rubbing of one part of the prosthesis against the shoulder, during the movements of rotation, particularly intra-rotation and extra-rotation.

According to another variant of the invention, the attachment means to attach the articulation device, particularly its second element, to the humerus consists of a shaft fixed to said second element, which is connected to the meta-epiphysiary part of the humerus.

According to another variant, the attachment means is made in a single piece with said second element of the articulation device, for example by extending in a suitable manner the lower part of the second element, or by adopting other attachment solutions.

BRIEF DESCRIPTION OF THE DRAWINGS

These and other characteristics of the present invention will become apparent from the following description of a preferential form of embodiment, given as a non-restrictive example with reference to the attached drawings wherein:

FIG. 1 is a front view of a humeral prosthesis according to the present invention, associated with a glenosphere;

FIG. 2 is a medial lateral view of the humeral prosthesis in FIG. 1 in the direction indicated by the arrow F in FIG. 1;

FIG. 3 is a perspective view of the humeral prosthesis in FIG. 1;

DETAILED DESCRIPTION OF A PREFERENTIAL FORM OF EMBODIMENT

Figure 4:
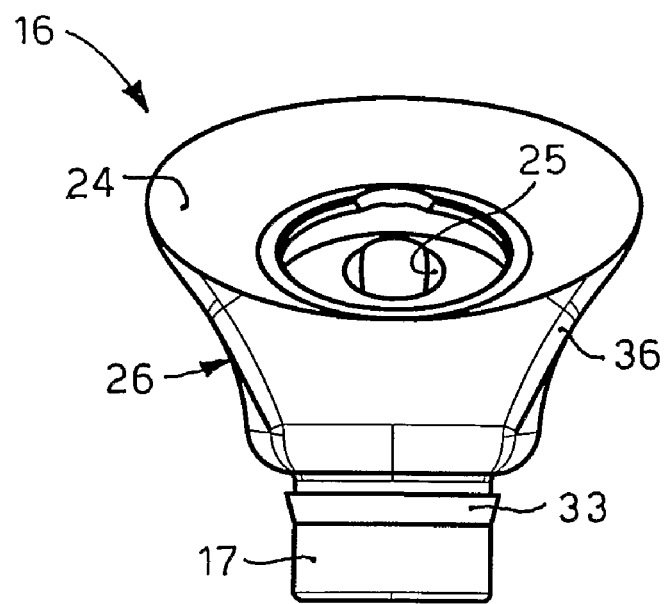
FIG. 4 is a medial lateral view of a part of the humeral prosthesis in FIG. 1.

With reference to FIG. 1, an inverse humeral prosthesis 10 comprises an articulation device 15 which is able to articulate with a corresponding glenosphere 12 made of polyethylene, fixed in the glenoid cavity, and to be fixed to the meta-epiphysary part of the humerus.

In the following description we shall refer mainly to an inverse prosthesis, but without excluding the application to an anatomical or normal prosthesis.

The articulation device 15 comprises an insert 16, made of polyethylene, pivoted around a pivoting axis Y to a humeral body 18, made of a cobalt-based alloy.

The device 15 also typically contains a connecting shaft 20 made of a titanium-based alloy, coaxial with the axis Y and fixed to the lower part of the humeral body 18. In particular, the shaft 20 has an end 19 with a determinate taper, for conical coupling with the humeral body 18.

In a known manner, the shaft 20 is able to be connected to the meta-epiphysary part of the humerus, so as to connect the articulation device 15 with the humerus.

The axis Y thus represents the axis around which the movements of ultra-rotation and extra-rotation of the humerus take place.

A rotation pin 22 is provided which functions as a rotation guide between the insert 16 and the humeral body 18, so that the whole is aligned with the axis Y, and which prevents the deformation of the polyethylene which makes up the insert 16. The pin 22 is able to be screwed into a seating 23 made on the end 19 of the shaft 20.

The insert 16 and the humeral body 18 have reciprocally complementary or congruent shapes, so as to be able to be coupled rotationally.

Figure 5:
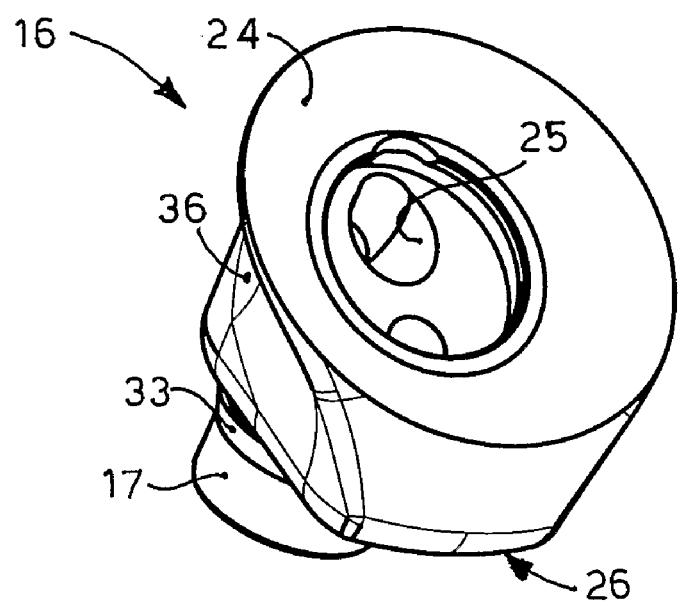
FIG. 5 is a perspective view of the part in FIG. 3.
Figure 6:
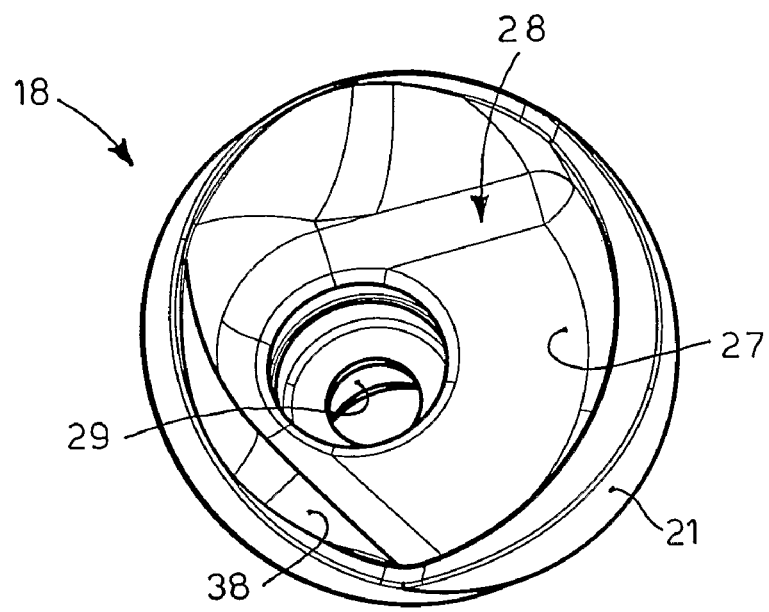
FIG. 6 is a perspective view of another part of the humeral prosthesis in FIG. 1.
Figure 7:
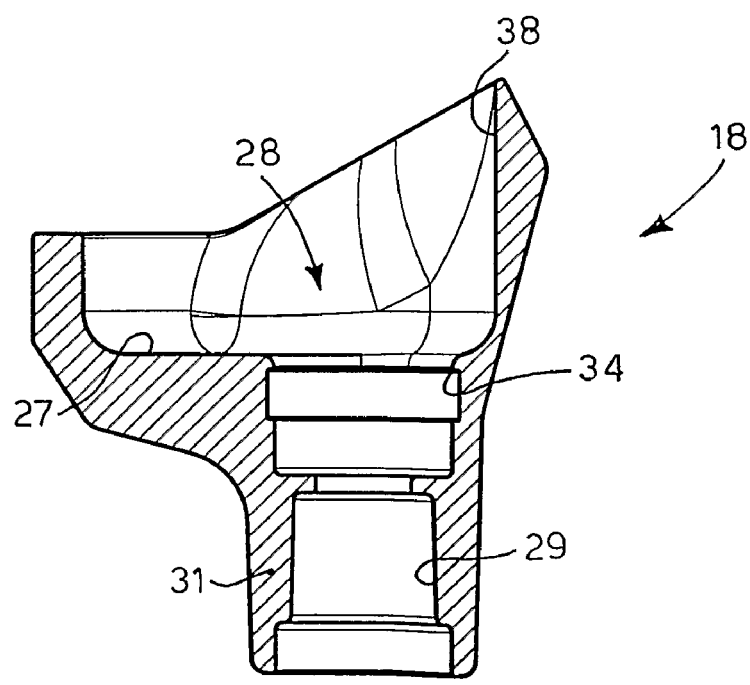
FIG. 7 is a front section of the part in FIG. 6.

The insert 16 and the humeral body 18 are represented individually respectively in FIGS. 4 and 5 and in FIGS. 6 and 7.

In the solution shown, both the insert 16 and the humeral body 18 have the shape of a flared cup, one of a size slightly different from the other, which develop around the axis Y.

In particular, the humeral body 18 has lateral walls 38 which delimit internally a concave seating 28 to locate the insert 16. The walls 38 are suitably shaped so as to have a curvilinear development around the axis Y and so as to be, axially, substantially vertical or slightly inclined and flared.

The humeral body 18 is provided at the lower part with a protuberance 31, in which a longitudinal through cavity 29 is made. In the through cavity 29 the conical coupling with the end 19 of the shaft 20 occurs.

The particular solution shown of the humeral body 18 is a cup cut transversely along an inclined plane as can be seen in FIG. 7, and with a barrier element, or containing edge 21, which has the function of at least partly covering the polyethylene and prevent or reduce the filling by fibrous tissue of the cavities and interstices of the device 15, once the prosthesis 10 has been implanted.

Figure 8:
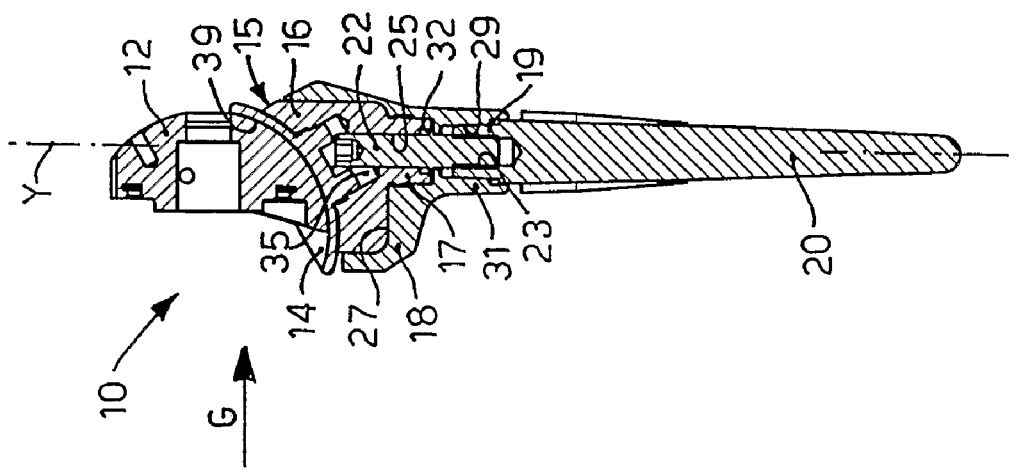
FIG. 8 is a front section of the humeral prosthesis in FIG. 1.

The insert 16, on an upper side, has a concave seating, or humeral seating 24, in which an articulation platelet 14 is housed and fixed (FIGS. 3, 8 and 9), made of an alloy based on cobalt, or titanium or ceramic, which during the normal use of the prosthesis 10 is interposed between the insert 16 and the glenosphere 12.

The platelet 14 mainly functions as an articulation interface between the device 15 and the glenosphere 12.

In particular, the platelet 14 has a concave external surface 39 (FIGS. 3, 8, 9 and 10) suitably shaped, for articulation with the glenosphere 12.

At the lower part, the platelet 14 has cylindrical pins 35, with a stabilizing function under load, inserted freely or with interference into the holes of the insert 16, to prevent accidental dis-assembly.

The presence of the platelet 14 is advantageous since, being made of metal, it determines a metal-plastic contact which allows the correct articulation of the polyethylene glenosphere 12 which otherwise would have to articulate on the insert 16, also made of polyethylene, with dangerous results for the articulation itself.

Advantageously, therefore, the platelet 14 is made of a material suitable for articulation with the glenosphere 12.

The platelet 14 also has the function, known for example from the patent application UD2004A000194 in the name of the present Applicant, of preventing or at least limiting the phenomenon of scapular notch, thanks to the anti-wear properties of the material of which it is made.

At the bottom, on the contrary, the insert 16 has a convex portion 26, suitable to be inserted rotatably into the concave seating 28 of the humeral body 18.

The convex portion 26 has a lateral surface 36, shaped so as to have a curvilinear development around the axis Y, coherent with the shaping of the walls 38 of the seating 28 and, on the side opposite the seating 24, has a protuberance 17 which is inserted into the through cavity 29 of the humeral body 18.

The protuberance 17 has an annular attachment tooth 33 able to cooperate with a corresponding attachment portion 34 of the cavity 29, to achieve a snap-in attachment and prevent an unwanted axial uncoupling of the insert 16 and the humeral body 18.

The protuberance 17 of the convex portion 26 has a through hole 25, through which said rotation pin 22 is inserted.

Once the humeral body 18 is coupled conically with the shaft 20, the pin 22 is inserted into the through cavity 29 and screwed into the seating 23 of the shaft 20. The pin 22 thus abuts axially with an abutment portion 32, on the bottom of the seating 28.

Subsequently, the insert 16 is housed rotatably in the seating 28 of the humeral body 18, taking care that the pin 22 also passes through the hole 25 made along the protuberance 17 of the insert 16. Above, the pin 22 does not interfere in rotation with the insert 16 or with the platelet 14. Therefore, the shaft 20, the pin 22 and the humeral body 18 are solidly associated with each other and are rotatable around the axis Y, with respect to the insert 16, in movements of intra-rotation and extra-rotation, as indicated by the arrow R in FIGS. 1 and 2.

In the solution shown, the rotation of the insert 16 and the humeral body 18 is limited to a determinate angular sector 27.

To this purpose, the lateral surface 36 and the walls 38 are suitably shaped in a complementary manner with respect to each other.

In particular, the lateral surface 36 of the insert 16 is axially flared, in a manner congruent with the walls 38 of the humeral body 18, with a slightly variable thickness or cross section.

In a variant, the surface 36 is substantially vertical with a constant section.

In the solution shown, the development in cross section, that is, around the axis Y, of the surface 36 and the walls 38 is substantially defined by two convergent segments, which can be rectilinear, concave or convex according to needs, and connected by a central curvilinear segment, as can be seen in FIGS. 5 and 6.

Both the surfaces 36 and the walls 38 are suitably beveled and joined, so as not to cause points of discontinuity or steps, which could impede the fluidity and naturalness of rotation.

According to the invention, when the humeral body 18 is driven rotationally, in the movements of intra-rotation and extra-rotation, the walls 38 abut on the corresponding surface 36 of the insert 16, limiting the rotation.

The surface 36 of the insert 16 thus constitutes an abutment portion and an impediment to the further rotation of the humeral body 18.

Figure 10:
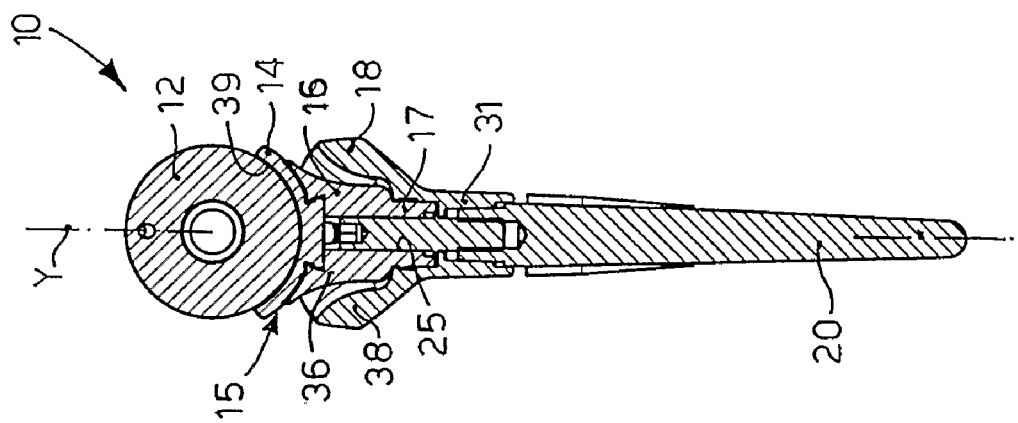
FIG. 10 is a second medial lateral section of the humeral prosthesis in FIG. 1 in the direction indicated by the arrow G in FIG. 8.
Figure 9:
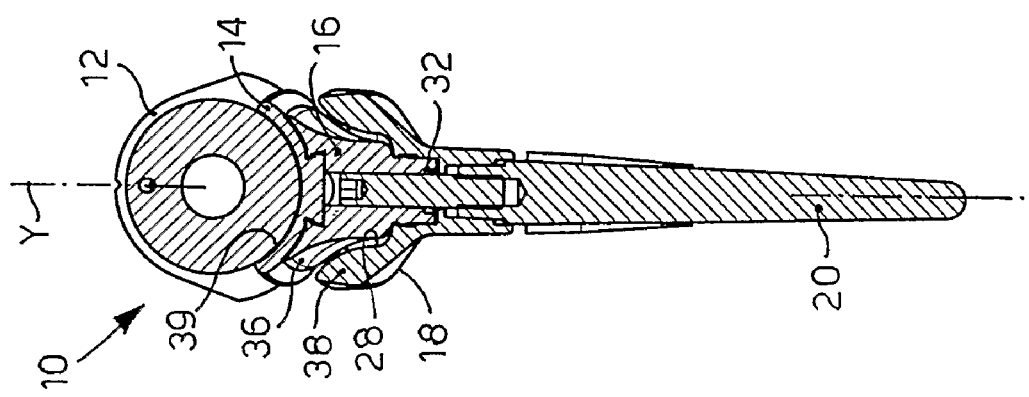
FIG. 9 is a first medial lateral section of the humeral prosthesis in FIG. 1 in the direction indicated by the arrow G in FIG. 8.

As can be seen from FIG. 6, and from FIGS. 9 and 10, which show sections relating to two parallel and offset planes, the section or thickness of the walls 38 is variable, increasing from the center towards the periphery, following the greater transverse inclination of the humeral body 18.

In this way, a geometry of the seating 28 is defined which delimits the determinate angular sector 27, as can be seen in FIG. 6.

The coupling of the protuberance 17 of the insert 16 and the hole 29 of the humeral body 18, and hence the pin 22, and the relative pivoting axis Y, are thus more displaced towards the periphery of the humeral body 18 with the larger inclination, making available for rotation the surface of the angular sector 27 towards the periphery of the humeral body 18 with lesser inclination.

The humeral body 18 is thus free to rotate, in a clockwise or anti-clockwise direction, in this determinate angular sector 27 which, in this case, has an amplitude of about 60°, that is, between +30° and −30°.

With a rotation of the humerus beyond the determinate angular sector 27, the walls 38 abut on the mating surface 36 and a further rotation in said direction causes the rotation, as a single body, of the humeral body 18 together with the insert 16, with the relative platelet 14.

Therefore, in cases of intra-rotation and extra-rotation of the humerus greater than about 30°, the traditional articulation of the articulation device 15 occurs with respect to the glenosphere 12.

Figure 11:
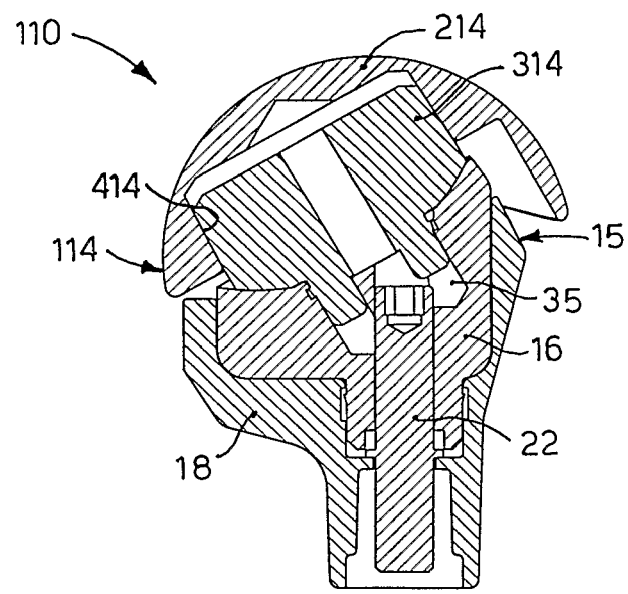
FIG. 11 is a front section of a variant of the prosthesis in FIG. 1.
Figure 12:
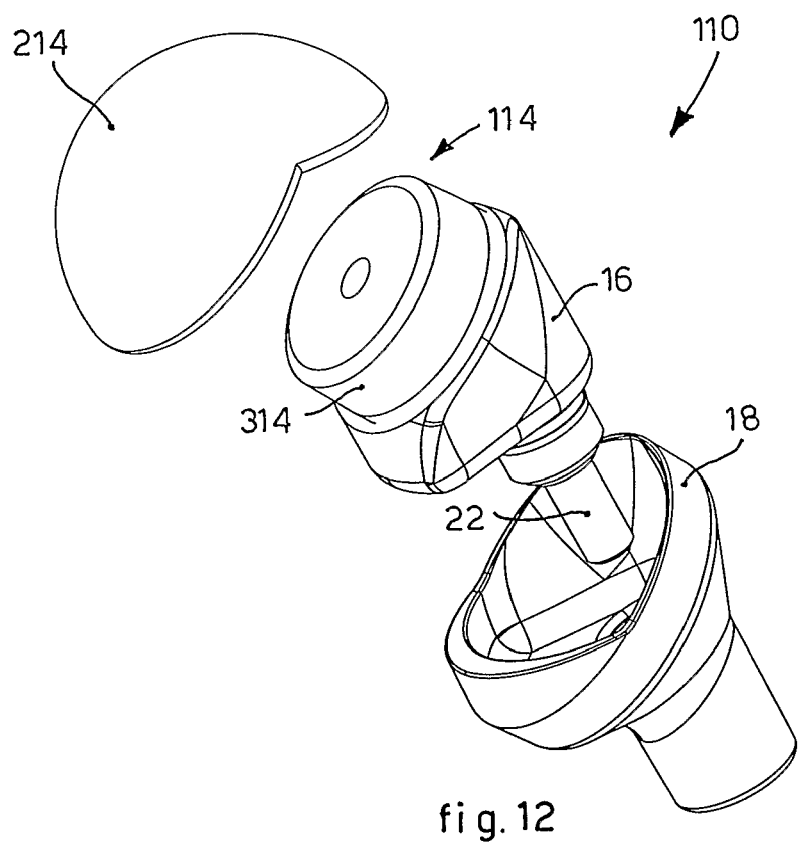
FIG. 12 is a perspective view in separate parts of a variant of the prosthesis in FIG. 1.

FIGS. 11 and 12 show as a variant the application of the present invention to a normal or anatomical prosthesis 110, in which the same reference numbers are used for parts equal to those of the solution shown in FIGS. 1 to 10. The prosthesis 110, unlike the prosthesis 10, provides that an artificial concave glenoid seating made of polyethylene, not shown here, is mounted on the glenoid cavity, whereas the articulation device 15 shown above is mounted on the humerus, in which, however, instead of the articulation platelet 14 an articulation member 114 is provided, at least partly convex.

The member 114 is formed by an at least partly spherical head 214, of shape and size coherent with the artificial glenoid seating for articulation therewith, and by a support element 314 by means of which the head 214 is connected to the insert 16. The support element 314 is coupled with the insert 16 substantially in the same way as the platelet 14 and the insert 16 are coupled, as already described. On the contrary, the support element 314 is connected to the head 214 by conical coupling of a conical part thereof with a mating cavity 414 of the head 214.

At least the head 214 is preferably made of cobalt-based alloy, for an effective articulation with the artificial glenoid seating.

Advantageously, the prosthesis according to the present invention can be configured both as an inverse prosthesis 10 and also as a normal prosthesis 110, simply by changing the articulation platelet 14 with the articulation member 114.

It is clear that modifications and/or additions of parts may be made to the humeral prosthesis 10, 110 as described heretofore, without departing from the field and scope of the present invention.

For example, the platelet 14, the articulation member 114 and the humeral body 18 can be made, at least partly, of a metal alloy based on titanium subjected to surface treatments of hardening, such as nitriding.

It is also clear that, although the present invention has been described with reference to some specific examples, a person of skill in the articulation shall certainly be able to achieve many other equivalent forms of humeral prosthesis, having the characteristics as set forth in the claims and hence all coming within the field of protection defined thereby.

The invention claimed is:

1. A humeral prosthesis for the articulation of a humerus in a scapula of a shoulder having a glenoid cavity, comprising
    an articulation device able to be associated both with an articulation element mounted on the glenoid cavity, and also at the top of said humerus by means of attachment means,
    wherein the articulation device is able to articulate with the articulation element, and the articulation device comprises an insert, made of plastic material, and a humeral body associated with said attachment means, and
    wherein the insert and the humeral body are pivoted to each other around a pivoting axis (Y) to allow a free but limited movement of intra-rotation and extra-rotation thereof around the pivoting axis (Y), and
    wherein the attachment means includes a shaft fixed to the humeral body and for connecting to the humerus along an axis coaxial with the pivoting axis (Y) of the insert and of the humeral body so the pivoting axis (Y) represents the axis around which the movements of intra-rotation and extra-rotation of the humerus take place.

2. The humeral prosthesis as in claim 1, wherein the articulation device comprises a first limiting element and a second limiting element able to cooperate with each other to define an angular sector that limits the reciprocal rotation of the insert and the humeral body.

3. The humeral prosthesis as in claim 2, wherein the angular sector has an amplitude comprised between about 30° and 90°.

4. The humeral prosthesis as in claim 2, wherein the angular sector has an amplitude comprised between about 50° and 70°.

5. The humeral prosthesis as in claim 1, wherein the insert comprises a convex portion and the humeral body comprises a concave portion in which the convex portion of the insert is able to be rotatably accommodated.

6. The humeral prosthesis as in claim 5, wherein the convex portion of the insert has a curvilinear shaped surface and the concave portion of the humeral body has a wall shaped in a manner at least partly mating with the curvilinear shaped surface.

7. The humeral prosthesis as in claim 6, wherein the curvilinear shaped surface and the wall are axially inclined and flared.

8. The humeral prosthesis as in claim 6, wherein the curvilinear shaped surface and the wall are substantially vertical.

9. The humeral prosthesis as in claim 6, wherein the articulation device comprises a first limiting element and a second limiting element for cooperating with each other to define an angular sector that limits the reciprocal rotation of the insert and the humeral body, and wherein the first limiting element comprises the curvilinear shaped surface and the second limiting element comprises the wall of the concave portion of the humeral body.

10. The humeral prosthesis as in claim 9, wherein the articulation element is at least partly convex, and wherein the insert is at least partly concave.

11. The humeral prosthesis as in claim 9, wherein the articulation device comprises an articulation platelet mounted on the insert and able to be disposed during use between the insert and the articulation element, the articulation platelet having a concave shape for articulation with the articulation element.

12. The humeral prosthesis as in claim 11, wherein the articulation platelet is made of a different material from the material of which the insert is made.

13. The humeral prosthesis as in claim 1, comprising pivoting means to pivot the insert to the humeral body.

14. The humeral prosthesis as in claim 1, wherein the articulation element is at least partly convex, and wherein the insert is at least partly concave.

15. The humeral prosthesis as in claim 1, wherein the articulation device comprises an articulation platelet mounted on the insert and able to be disposed during use between the insert and the articulation element, the articulation platelet having a concave shape for articulation with the articulation element.

16. The humeral prosthesis as in claim 15, wherein the articulation platelet is made of a different material from the material of which the insert is made.

17. The humeral prosthesis as in claim 1, wherein the articulation element is at least partly concave, and wherein the insert is at least partly convex, and
  wherein the articulation device comprises an articulation member disposed during use between the insert and the articulation element, which is formed by an articulation head, convex in shape, for the articulation of the articulation element and mounted on a support element, in turn mounted on the insert.

18. The humeral prosthesis as in claim 17, wherein the support element is made of a different material from the material of which the articulation element is made.

19. A prosthesis for the articulation of a humerus in a scapula of a shoulder having a glenoid cavity, comprising:
  an articulation element for mounting on the glenoid cavity and comprising a glenosphere;
  an articulation device for associating with the articulation element, the articulation device comprising an insert and a humeral body, the insert made of plastic material;
  the insert on an upper side has a concave seating in which an articulation platelet is housed and fixed for interposing during normal use between the insert and the glenosphere, the platelet having a concave external surface shaped for articulation with the glenosphere;
  wherein the insert, at the bottom of the insert, comprises a convex portion and the humeral body has a concave seating for rotatably accommodating the convex portion of the insert, wherein the convex portion of the insert has a curvilinear shaped surface and the concave seating of the humeral body has a wall shaped in a manner at least partly mating with the curvilinear shaped surface,
  wherein the insert and the humeral body are pivoted to each other around a pivoting axis (Y) to allow a free but limited movement of intra-rotation and extra-rotation thereof around the pivoting axis (Y), and
  portion of the humeral body distal to the concave seating comprising attachment means for attaching to a top portion of the humerus;
  wherein the attachment means comprises a shaft fixed to the humeral body and for connecting to the humerus along an axis coaxial with the pivoting axis (Y) of the insert and of the humeral body so the pivoting axis (Y) represents the axis around which the movements of intra-rotation and extra-rotation of the humerus take place;
  wherein when the prosthesis is assembled and attached to the glenoid cavity and humerus, with the articulation element in an upright position with its glenosphere facing away from the glenoid cavity, the articulation element, the insert, the humeral body and the shaft are coaxial along the pivoting axis (Y).

20. The humeral prosthesis of claim 19, wherein the humeral body is provided at a lower part with a protuberance having a longitudinal through cavity for coupling with an end of the shaft to fix the shaft to the humeral body.

* * * * *